United States Patent [19]

Menocal, Jr.

[11] Patent Number: 5,607,451
[45] Date of Patent: Mar. 4, 1997

[54] FLAT TWEEZERS

[75] Inventor: Serafin G. Menocal, Jr., Fair haven, N.J.

[73] Assignee: Mind Mechanics, Inc., Red Bank, N.J.

[21] Appl. No.: 954,661

[22] Filed: Sep. 30, 1992

[51] Int. Cl.⁶ .................................................. A61B 17/30
[52] U.S. Cl. ........................ 606/210; 294/99.2; 606/131
[58] Field of Search .................................. 606/210, 131, 606/51, 52; 294/99.2

[56] References Cited

U.S. PATENT DOCUMENTS

| | | | |
|---|---|---|---|
| 950,499 | 3/1910 | Wells | 606/210 X |
| 3,367,336 | 2/1968 | Eizenberg | 606/210 |
| 3,392,727 | 7/1968 | Hanlon | 606/210 |
| 3,589,369 | 2/1969 | Alksnis . | |
| 4,637,236 | 1/1987 | Almblad . | |
| 4,976,718 | 12/1990 | Daniell | 606/210 X |

*Primary Examiner*—Michael H. Thaler
*Attorney, Agent, or Firm*—Kane, Dalsimer, Sullivan, Kurucz, Levy, Eisele and Richard

[57] ABSTRACT

A flat tweezer formed of a folded plastic material which can be opened to lay flat within the case. The tweezer may be formed from a plastic card with score lines defining the tweezer arms and a hinge coupling the arms.

14 Claims, 5 Drawing Sheets

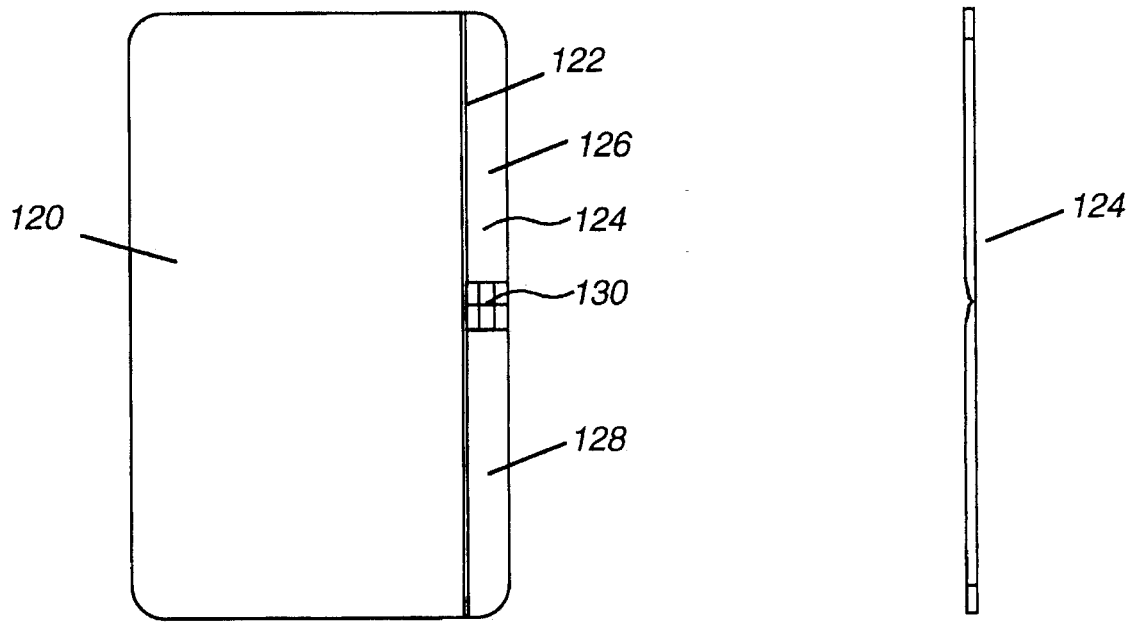
Fig. 9.  Fig. 10.
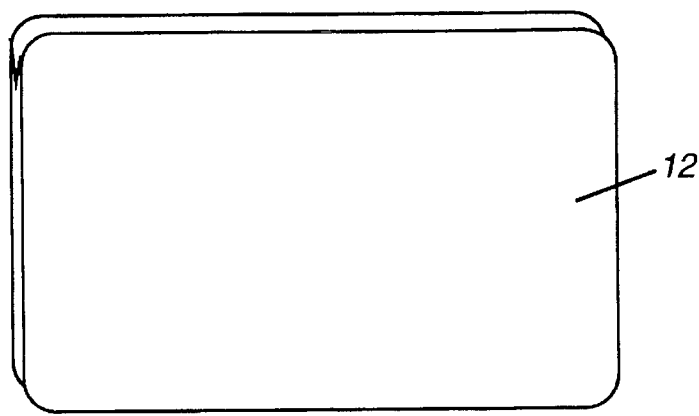
Fig. 11.

FLAT TWEEZERS

BACKGROUND OF THE INVENTION a. Field of Invention

The invention pertains to planar tweezers having a flat configuration which are particularly suited for inclusion into a flat credit card sized case such as a first aid kit, a cosmetic case, and so on.

b. Description of the Prior Art

One important implement in medical kits, especially for medical kits designed for treatment of insect bites, such as ticks, is a tweezer used to remove the insect, an insect sting and so on. In addition, tweezers are frequently used for various other medical or cosmetic purposes and are frequently included in cosmetic kits. However, until now tweezers have been made of metal, are relatively large and heavy and accordingly contribute significantly to the overall size of the kits.

OBJECTIVES AND SUMMARY OF THE INVENTION

An objective of the present invention is to provide a tweezer which is relatively flat when not used so that it can be easily stored and carried, for example as part of a medical kit.

A further objective is to provide a tweezer made of material using relatively inexpensive manufacturing processes such as molding, stamping and so on.

Other objectives and advantages of the invention shall become apparent from the following description.

Briefly, a tweezer constructed in accordance with this invention consists of a pair of arms coupled by hinge means. Preferably, the arms and hinge are defined by score lines on a plastic blank, and are broken out for use as required.

BRIEF DESCRIPTION OF THE DRAWINGS

FIG. 9 shows a top view of a third alternate embodiment of the tweezer;

FIG. 10 shows a side view of the tweezer of FIG. 9; and

FIG. 11 is a side perspective view of a case.

DETAILED DESCRIPTION OF THE INVENTION

Figure 1:
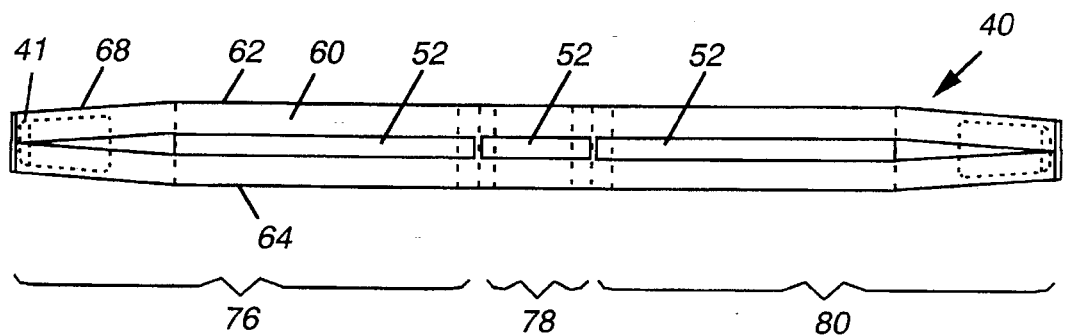
FIG. 1 shows a top view of a tweezer constructed in accordance with this invention.
Figure 2:
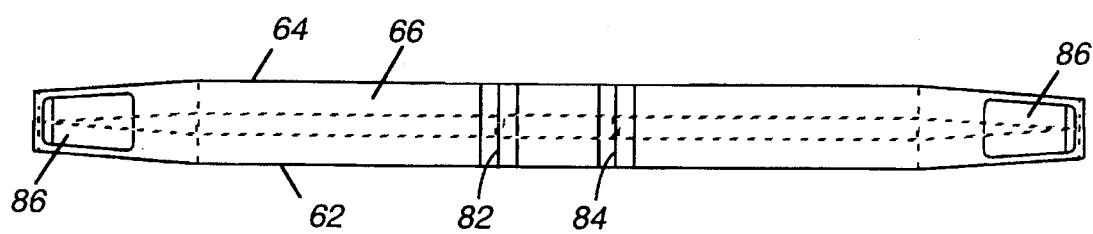
FIG. 2 shows a bottom view of the tweezer of FIG. 1.
Figure 3:
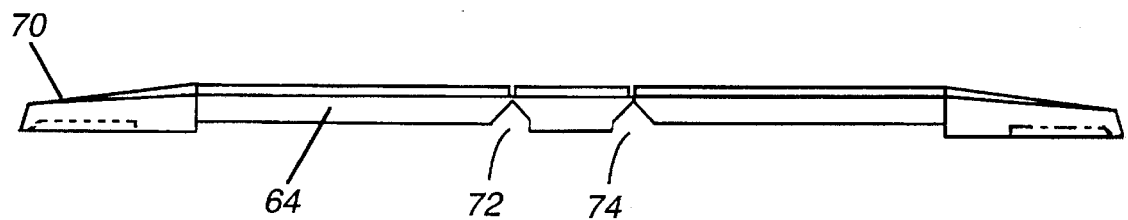
FIG. 3 shows a side view of the tweezer of FIGS. 2 and 3.
Figure 4:
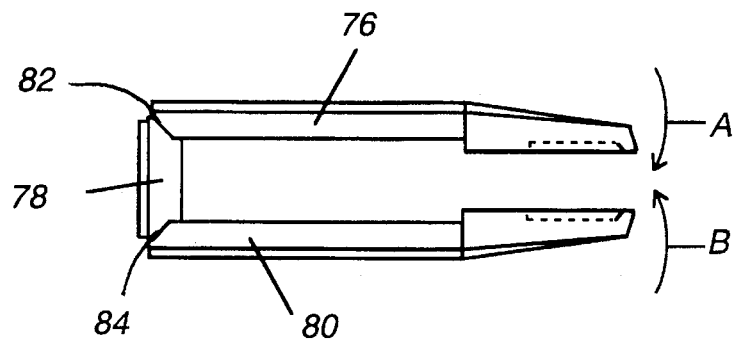
FIG. 4 shows a side view of the tweezer of FIGS. 1-3 in the closed position.
Figure 5:
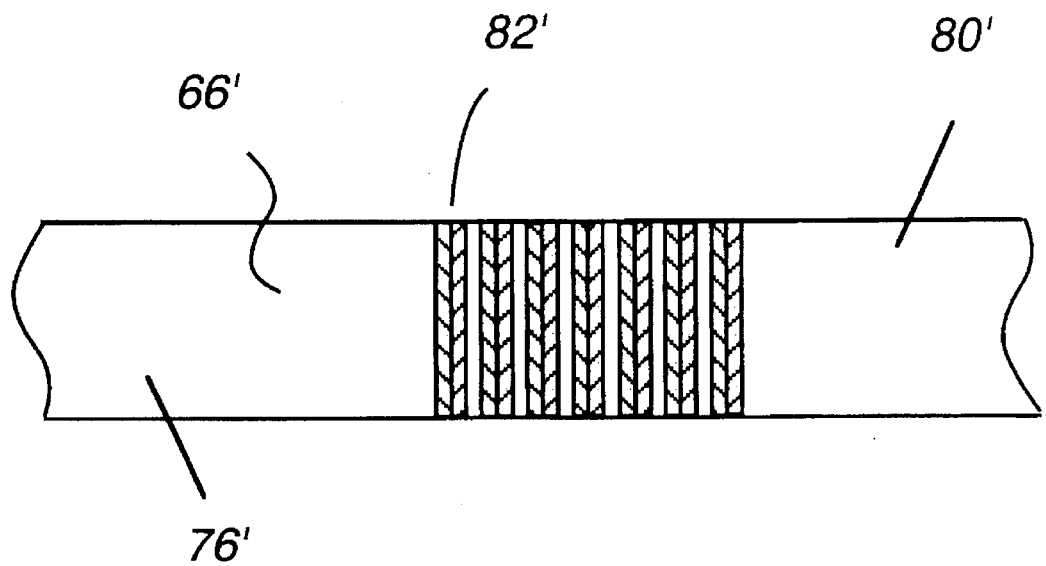
FIG. 5 shows a bottom view of an alternate embodiment of the tweezer of FIG. 4 in the closed position.
Figure 6:
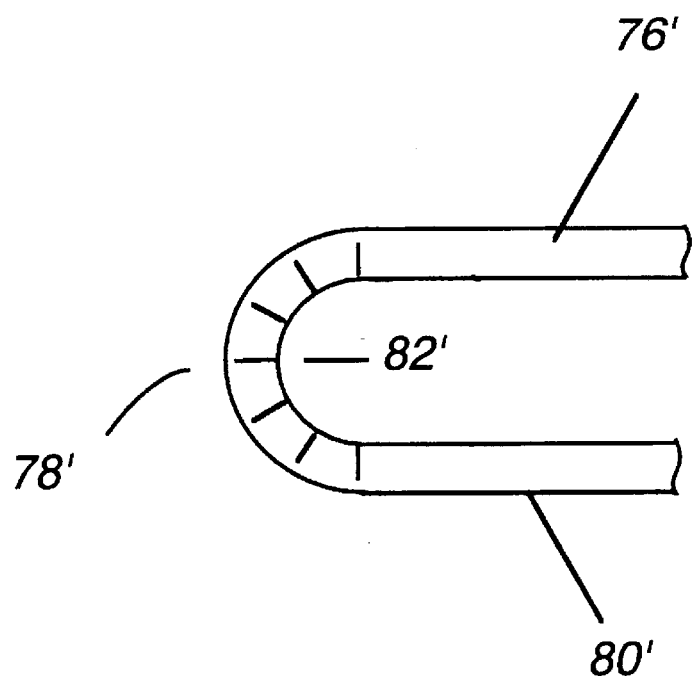
FIG. 6 shows a side view of the tweezer of FIG. 5 in the closed position.

FIGS. 1–4 show details of a tweezer 40 constructed in accordance with the present invention particularly suited for inclusion in medical or cosmetic kit. Preferably, the tweezer 40 is made of a single piece of flat elongated molded plastic 41. As seen in the Figures piece 41 includes a top surface 60, two side surfaces 62, 64, and a bottom surface 66. The top and bottom surfaces are tapered at both ends as at 68 (FIG. 1) and 70 (FIG. 3). On the bottom surface 66 there are two notches 72, 74 extending in parallel transversely across the tweezer. Preferably, these notches are defined by cuts made at an angle of 45° with respect to surface 66. These two notches partition the piece 41 into two tweezer arms 76, 80 and an intermediate section 78, separated by living hinges 82, 84. Alternately, as shown in FIG. 5, bottom surface 66' may be provided with a plurality of parallel side lines 82' shallower than cuts 72, 74. Some lines 82' form a continuous living hinge between the arms of the tweezer, as shown in FIG. 6.

As shown in FIG. 1, top surface 60 is provided with ridges 52 extending along the sections. Ridges 52 provide stability for the sections, and insure that the sections do not bend too much when a force is applied thereto. The notches used to form the living hinges also act as mechanical stops to limit the angular movement of the tweezer arms.

At the two longitudinal ends on surface 66, piece 41 is provided with two depressions 86.

Advantageously, the tweezer of FIGS. 1–3 can be stored in the open position in a flat configuration in which the two arms and the hinge substantially co-planar. For use, the arms are folded at the notches into the shape shown in FIG. 4. The springiness of the film hinges 82, 84 and the flexibility of the arms 76, 80 permit the two ends to be pivoted toward each other as shown by arrows A and B to thereby grasp an object therebetween. If the object is fragile and must grasped without damaging it, the tweezer is positioned so that the object grasped is surrounded or enclosed by the depressions 86 in arms 76, 80.

Figure 7:
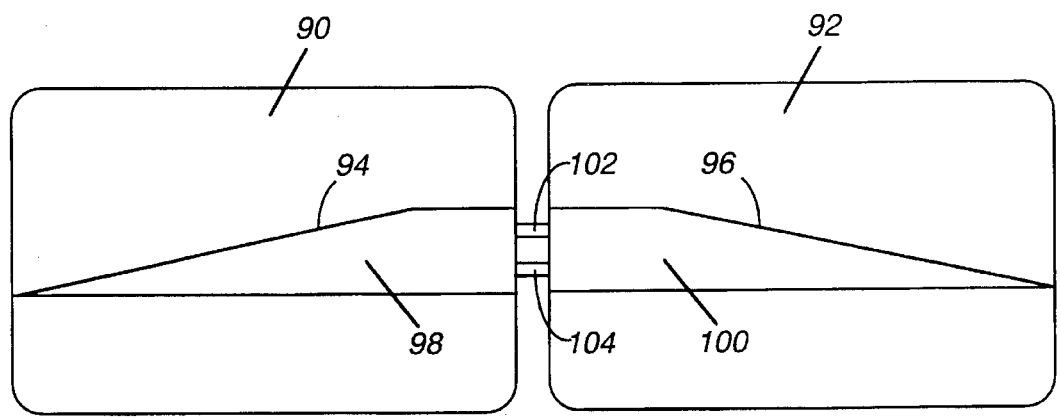
FIG. 7 shows a top view of a first alternate embodiment of the tweezer.

FIGS. 7–10 show alternate embodiments of the tweezer. In FIG. 7 two blank cards 90, 92 made of a plastic material are provided with score lines 94, 96 defining the two tweezer arms, 98 and 100. The two cards are joined by film hinges 102, 104 to permit the two cards 90, 92 to be folded over each other. In the folded configuration, the cards can be stored inside or next to case 12. When tweezers are required, the cards 90, 92 are removed and the tweezer arms are broken out along respective score lines 94, 96. The two arms are now joined by live film hinges 102, 104.

Figure 8:
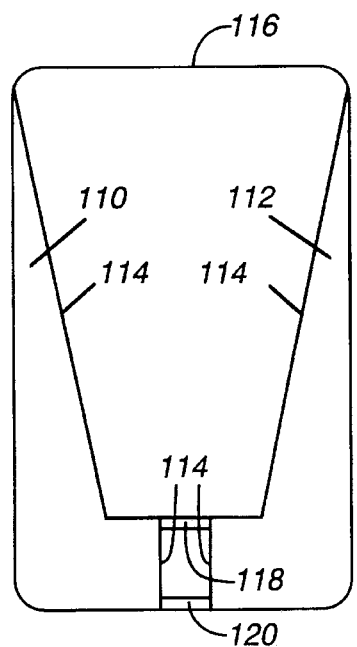
FIG. 8 shows a top view of a second alternate embodiment of the tweezer.

In the embodiment of FIG. 8, the L-shaped arms 110, 112 of the tweezer are defined by score lines 114 on a single plastic card 116. The two arms 110, 112 are joined by two live hinges 118, 120. The card 116 is again carried inside or adjacent to case 12 and the tweezer is broken out of card 116 as required.

In the embodiment of FIGS. 9 and 10 a flat card 120 is provided having along one edge a score line 122 defining a tweezer 124. Tweezer 124 is formed of two arms 126, 128 joined by a film hinge 130. Card 120 is carried in a wallet inside or adjacent to case 12. When required the tweezer 124 is torn off from the card 120 along score line 122.

Obviously numerous modifications may be made to the invention without departing from its scope as defined in the appended claims.

I claim:

1. A tweezer comprising:

a piece of flat plastic material, said plastic material including a plurality of living hinges comprising V-shaped notches of reduced thickness of material with said notches located on one side of the material partitioning said flat piece of material into two tweezer arms, said arms being pivotable about said hinges.

2. The tweezer of claim 1 wherein said two tweezer arms are separated by an intermediate section.

3. The tweezer of claim 2 wherein said living hinges form mechanic stops for limiting the angular movement of one of said arms with respect to said intermediate section.

4. The tweezer of claim 1 wherein said piece has a top surface and two opposing ends, said top surface being formed with recesses at said ends arranged to hold an insect body without crushing said body when said arms are closed.

5. A blank for making tweezer, said blank comprising:

a card made of a flat plastic material, said card having at least one score line arranged to form a tweezer when broken.

6. The blank of claim 5 wherein said card has a generally rectangular shape.

7. The blank of claim 5 wherein said card has first and second opposed longitudinal sides, and is formed with a first score line defining a first tweezer arm with said first longitudinal side and a second score line defining a second tweezer arm with said second longitudinal side.

8. The blank of claim 7 wherein said tweezer arms are connected by hinge means for flexing said tweezer arms when said tweezer is broken out of said card.

9. The blank of claim 7 wherein said arms are L-shaped.

10. The blank of claim 5 wherein said card has a longitudinal side and said score line is parallel to said longitudinal side to define with said longitudinal side a first tweezer arm and a second tweezer.

11. The blank of claim 10 wherein said tweezer arms are connected by hinge means for flexing said arms when said tweezer is broken out of said card.

12. The blank of claim 5 wherein said card is credit-card sized.

13. A flat tweezer comprising:

first and second flat arms made of a plastic material; and a plurality of living hinges comprising V-shaped notches of reduced thickness of material connecting said arms, wherein said arms are movable between a flat position wherein said arms are substantially coplanar, and a bent position wherein said arms are in an opposing relationship.

14. The tweezer of claim 13 wherein said arms are disposed along a common longitudinal axis in said flat position.

* * * * *